United States Patent [19]

Martin et al.

[11] Patent Number: 4,761,426

[45] Date of Patent: * Aug. 2, 1988

[54] LYSOCELLIN-CONTAINING COMPOSITION AND PROCESS FOR PROMOTING GROWTH AND FEED EFFICIENCY OF FOOD PRODUCING ANIMALS

[75] Inventors: Jerome L. Martin; David R. Bright; Robert D. Williams; Vernon V. Young, all of Terre Haute, Ind.

[73] Assignee: International Minerals & Chemical Corp., Terre Haute, Ind.

[*] Notice: The portion of the term of this patent subsequent to Mar. 31, 2004 has been disclaimed.

[21] Appl. No.: 643,763

[22] Filed: Aug. 24, 1984

Related U.S. Application Data

[63] Continuation of Ser. No. 291,134, Aug. 7, 1981, abandoned, which is a continuation-in-part of Ser. No. 196,722, Oct. 8, 1980, abandoned.

[51] Int. Cl.$^4$ .............................................. A61K 31/35
[52] U.S. Cl. .................................................... 514/460
[58] Field of Search .......................................... 514/460

[56] References Cited

U.S. PATENT DOCUMENTS

| | | | |
|---|---|---|---|
| 3,705,238 | 12/1972 | Hammill et al. | 424/121 |
| 3,794,732 | 2/1974 | Raun | 424/283 |
| 3,839,557 | 9/1974 | Raun | 424/115 |
| 4,033,823 | 7/1977 | Liu . | |
| 4,129,578 | 7/1978 | Celmer et al. | 260/345 |
| 4,148,890 | 4/1979 | Czok et al. | 424/181 |
| 4,161,520 | 7/1979 | Osborne et al. | 424/285 |
| 4,218,443 | 8/1980 | Comai et al. | 424/181 |
| 4,305,956 | 12/1981 | Shibuya et al. | 424/283 |

OTHER PUBLICATIONS

Hammond et al–J. An. Sci., vol. 51, No. 1, Jul. 1980, pp. 207–214.
Westley, J. W.: Polyether Antibiotics: Versatile Carboxylic Acid Ionophores Produced by Streptomyces, Advances in Applied Microbiology 22:177–223, 1977.
Ebata, E. et al: Lysocellin, A New Polyether Antibiotic, Journal of Antibiotics 28(2):118–121, 1975.
Otake, N. et al: The Assignment of the $^{13}$C—NMR Spectrum of Lysocellin and Its Biosynthesis, Agric. Biol. Chem. 42(10):1879–1886, 1978.
Otake et al., J.C.S. Chem. Comm., 1975, pp. 92–93.
Mitani et al., The Journal of Antibiotics, vol. 30, Mar. 1977, pp. 239–293.

Primary Examiner—Sam Rosen
Attorney, Agent, or Firm—Bernard, Rothwell & Brown

[57] ABSTRACT

A growth promoting and feed efficiency-enhancing amount of a lysocellin material selected from the group consisting of lysocellin, lysocellin free acid, and the physiologically acceptable salts thereof is administered to a food-producing animal selected from the group consisting of ruminants, swine and poultry in a process for promoting growth and enhancing feed efficiency of such a food-producing animal. A feed supplement for a food-producing animal, the feed supplement being capable of increasing the rate of growth of the animal when supplied in the animal's feed on a regular basis during the animal's normal growth period, and which is also capable of enhancing feed efficiency of the animal, includes a mixture of a basal feed material for a food-producing animal selected from the group consisting of ruminants, swine and poultry, and a growth rate-increasing and feed efficiency-enhancing amount of a lyoscellin material selected from the group consisting of lysocellin, lyoscellin free acid, and the physiologically acceptable salts thereof.

15 Claims, No Drawings

LYSOCELLIN-CONTAINING COMPOSITION AND PROCESS FOR PROMOTING GROWTH AND FEED EFFICIENCY OF FOOD PRODUCING ANIMALS

RELATED APPLICATIONS

This is a continuation of application Ser. No. 291,134, filed Aug. 7, 1981, now abandoned, which was a continuation-in-part of copending application Ser. No. 196,722 filed Oct. 8, 1980 now abandoned.

BACKGROUND OF THE INVENTION

The present invention relates to an animal growth promoting process which utilizes certain forms of lysocellin as a growth-promoting substance in food-producing mammals.

A fairly comprehensive review of the various classes of polyether antibiotics is set forth in Westley, *Adv. Appl. Microbiology* 22, 177–223 (1977). Lysocellin falls into Class 2a as defined by Westley. Class 2a comprises divalent polyethers of a linear configuration which may contain from about two or about three tetrahydropyran and/or furan structures, up to three total ring structures and no nitrogen atoms. Table VIII of the Westley publication discloses the effective level of lysocellin as a coccidiostat. Lysocellin at 300 ppm in feed was said to be effective against *Eimeria tenella*. The reference refers to the use of lysocellin in poultry feed, and the level of lysocellin required to function as a coccidiostat considerably greater than other polyether antibiotics, such as monensin, nigericin, lasalocid and others.

Lysocellin was first reported in the literature by Ebata, et al, *The Journal of Antibiotics* 28(2):118–121, 1975. The physico-chemical properties of lysocellin are described there, including a melting point of about 158°–160° C. of the colorless needles of the sodium salt. The antibiotic is said to be produced from a mutant strain of *Streptomyces cacaoi* var. *asoensis* designated *Streptomyces cacaoi* var. *asoensis* K-9 Met-, but this strain has apparently not been made available to the public. This reference discloses that lysocellin is active against gram-positive bacteria, antibiotic resistant *Staphylococcus aureus*, some fungi, but that it is not active against gram-negative bacteria. There is no disclosure here of any use of lysocellin in meat-producing animals.

The structural formula for lysocellin was set forth by Otake, et al, *Agric. Biol. Chem.* 42(10): 1879–1887, 1978. This reference also reports that lysocellin is effective in treating coccidial infections in poultry, but there is no mention here of any other use of lysocellin in meat-producing animals.

U.S. Pat. No. 4,033,823 issued July 3, 1977, to Liu, et al, discloses the structural formula of lysocellin and a method for making it using *Streptomyces longwoodensis* (ATCC 29251). This patent only describes the use of lysocellin as an antimicrobial.

More recently, lysocellin was compared to a number of other polyether antibiotics for inhibition of ruminal degradation of L-tryptophan (TRP) to 3-methylindole (3MI) in vitro. Other polyether antibiotics used for the comparison included desoxysalinomycin, X-206, nigericin, lasalocid, monensin, narasin and salinomycin. Chloral hydrate was also used. The study was aimed at determining the potential effect of these antibiotics in the treatment of acute bovine pulmonary edema and emphysema (ABPE), or "fog fever", which appears to relate to ruminal production of 3MI. Hammond, et al, *Journal of Animal Science* 51(1): 207–214, 1980.

The above study by Hammond, et al, reported that the polyether antibiotics tested were the most effective compounds in reducing in vitro ruminal degradation of TRP to 3MI without significant decrease in VFA production. However, lysocellin was reported as one of the least effective of the polyether antibiotics tested for this purpose. This publication concludes that "further investigations of the effects of monensin on live animals are warranted". No further work with lysocellin was recommended by the authors. It should be noted that monensin did depress the VFA production in this test, and that its use as a feed additive is only for improved feed efficiency or utilization. See: U.S. Pat. No. 3,839,557.

U.S. Pat. No. 4,129,578 discloses the use of Compound 38,295 (etheromycin) as having anticoccidial, antimicrobial and growth promotant properties. Various cationic salts of etheromycin are disclosed, including copper, zinc, ammonium, calcium, magnesium and lithium salts. However, the microorganism, *Streptomyces hygroscopicus* ATCC 31050 used in the above reference has been withdrawn from the culture collection, so the reference is not believed to be "enabling" as to the growth promoting effects disclosed. In any event, the patent discloses only the use of etheromycin (Antibiotic 38,295 derived from ATCC 31050).

Recently issued U.S. Pat. No. 4,221,724 Liu et al, discloses the use of polyether antibiotic X-14766A as a growth promotant for ruminants. However, the only results reported in this patent were for in vitro volatile fatty acid production. Although such tests may give an indication that a substance will be effective as a growth promotant in ruminants, this is not conclusive, and actual in vivo testing is necessary. The molecular structure of X-14766A is different from lysocellin. X-14766A includes a chloride group on a methylbenzoic acid group, there are forty-three carbon atoms in the molecule, and there are four successive heterocyclic polyether rings, whereas lysocellin contains only two successive heterocyclic polyether rings, contains neither chloride groups, nor a methylbenzoic acid group. In addition, lysocellin has a total of only thirty-four carbon atoms in the molecule.

It has now been surprisingly discovered that the various forms of lysocellin act as especially effective growth-promoting and feed efficiency-enhancing agents when administered to food-producing mammals such as ruminants. In ruminants having a developed rumen function, including cattle, sheep and goats, the various forms of lysocellin are believed to promote growth and enhance the efficiency of feed utilization in the animal by lowering the acetate/propionate ratio among the volatile fatty acids (VFA) found in the animal's rumen fluid. The relationship between acetate/propionate ratio in the rumen and feed efficiency in the ruminant animals is explained in greater detail in Raun, U.S. Pat. No. 3,794,732 issued Feb. 26, 1974.

Therefore, the present invention relates to processes for promoting growth and enhancing feeding efficiency in food-producing mammals by administering various forms of lysocellin to meat-producing animals, particularly ruminants. Among the useful forms of lysocellin are: the free acid and the pharmaceutically acceptable salts, including sodium, zinc, manganese, magnesium and copper salts. Zinc, manganese and copper are believed to form salt "complexes", and two of the linear polyether molecules "wrap" around the bivalent cation.

In accordance with the present invention, the zinc, manganese, or copper complexes of lysocellin can be formed by adding water-soluble zinc, manganese or copper salts to the fermentation broth in which lysocellin has been prepared, and the resulting broth-insoluble zinc, manganese or copper complexes of lysocellin can then be recovered from the broth and employed as growth-promoting and feed efficiency enhancing additives, especially in feed for food-producing mammals such as ruminants, swine and poultry.

Lysocellin-containing fermentation broth is prepared in conventional manner by fermenting a nutrient-containing liquid fermentation medium inoculated with a *Streptomyces longwoodensis* (ATCC 29251) which is capable of producing lysocellin. Suitable liquid fermentation media are generally aqueous dispersions containing a nitrogen source and a carbohydrate source. Nitrogen sources for use in the fermentation media herein can include, for example, sugar, molasses, cornsteep liquor and the like. The fermentation media can also contain a variety of optional ingredients, if desired, such as for example, pH adjustment agents, buffers, trace minerals, antifoam agents, filter aids, etc.

The Streptomyces microorganism is grown in an aerated, agitated, submerged culture with the pH of the broth adjusted to about neutral, i.e., from a pH value of about 6.5 to about 7.5. Fermentation can generally be carried out at slightly elevated temperatures, e.g., between about 25° C. and 35° C. Incubation of the broth can be carried out for a period of several days, e.g., from about 4 to 6 days or longer if it is economically advantageous to do so.

A particular method for producing the antibiotic lysocellin was disclosed by Liu et al in U.S. Pat. No. 4,033,823 by the cultivation of a strain of *Streptomyces longwoodensis* which is on unrestricted deposit at the American Type Culture Collection under the designation ATCC 29251. The structure of lysocellin is as follows:

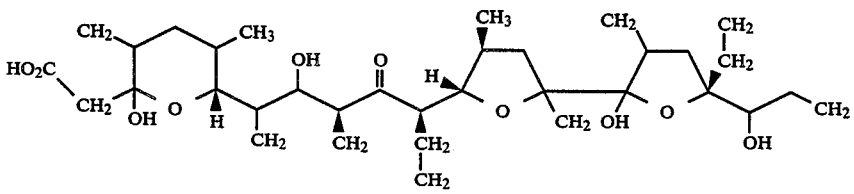

Suitable methods for preparing the lysocellin antibiotic are set forth in the above-mentioned patent. The characteristics of lysocellin were first set forth in the article by Ebata et al, *J. Antibiotics* 28:118-121, 1975.

The various forms of lysocellin, including the free acid, sodium salts, and the zinc, manganese, and copper lysocellin complexes used in the present invention act as growthpromoting agents in food-producing mammals, e.g., ruminants, swine and poultry. These forms of lysocellin can be administered to food-producing animals, either orally, subcutaneously or parenterally, in amounts sufficient to enhance the growth rate of the animal. The amount of the lysocellin material administered to an animal varies, of course, with the species of animal, the desired rate of growth, and the like. The material is frequently administered to ruminants in an amount of about 1 to 200, preferably about 1 to 50 milligrams per head per day.

Preferably, the lysocellin material is administered to food-producing animals in their feed, and can be conveniently added to animal feed in the form of the dried, antibiotic-containing biomass which is recovered as a feed additive composition from the fermentation broth as hereinbefore described. It may also be administered in liquid feeds, and in the animal's drinking water.

A feed composition may be prepared containing the usual nutritionally-balanced quantities of carbohydrates, proteins, vitamins and minerals as diluents together with the lysocellin material. Some of the usual sources of these dietary elements are grains, such as ground grain and grain by-products; animal protein substances, such as those found in fish meal and meat scraps; vegetable proteins, such as soybean oil meal or peanut oil meal; vitaminaceous materials, e.g., mixture of vitamins A and D, riboflavin supplements and other vitamin B complex members; and bone meal and limestone to provide minerals. A type of conventional feed material for use with cattle, for example, includes alfalfa hay and ground corn cobs, together with supplementary vitaminaceous substances if desired. The lysocellin materials of the present invention can generally be employed in the feed compositions to the extent of from about 15 grams per ton to 200 grams per ton, preferably from about 75 grams per ton to 125 grams per ton.

The lysocellin growth-promoting agents described herein, can also be administered to food-producing animals subcutaneously or parenterally in combination with a pharmaceutically-acceptable carrier. For example, the lysocellin materials can be employed in an injection composition, or as an implant under the skin. Administration of the growthpromoting agents herein in this manner can include intramuscular, intravenous, subcutaneous, and intraperitoneal injections. When an implant is used, for example, a ball or cylindrical implant inserted under the skin on the ear of an animal, the implant will generally contain from about 1 mg to 100 mg of one of the lysocellin materials.

The various lysocellin materials, their preparation and recovery and the feed and feed additive compositions involved in the present invention as well as their usefulness as growth promoting agents for ruminants are illustrated by the following examples. Such examples include the preparation, recovery and evaluation of the preferred lysocellin material, but are in no way limiting of the present invention to processes involving that particular material.

EXAMPLE I

Crystalline sodium lysocellin was produced following the fermentation method set forth in Example 1 of U.S. Pat. No. 4,033,823 issued July 5, 1977, which procedure is incorporated herein by reference. The melting point of the resultant crystalline sodium lysocellin isolated from the fermentation broth was 159.6° (Mettler). Infra-red spectrum and optical rotation agree with the date for sodium lysocellin published by Otake, et al, op. cit. NMR spectra and elemental analysis of the crystalline material obtained by the above method confirmed that the product was sodium lysocellin.

EXAMPLE II

Sodium lysocellin produced by the method of Example I was used to make the free acid of lysocellin as follows:

3.9 g sodium lysocellin @(0.006 moles) and 1.4 g zinc acetate hydrate [Zn(Ac)$_2$.2H$_2$O] @(.006 mole) were mixed together in 30 ml denatured ethanol (3A). The sodium lysocellin was first suspended in the ethanol and stirred, and the sodium acetate hydrate was added, and the suspension stirred at room temperature until everything was dissolved. The pH was then adjusted to a range of 2-4, with 37% HCl. Stirring was continued for 20-30 minutes until precipitation of a birefringent material started. Precipitation was continued by adding water dropwise (holding pH at 4) until about 60 ml of water was added. The resulting crystalling precipitate of the free acid of lysocellin was isolated and dried. The resulting free acid of lysocellin comprised birefringent crystals.

The above material was again dissolved in ethanol and recrystallized from ethanol by again adding water dropwise until the free acid of lysocellin precipitated out as birefringent crystals. The melting point of this material was 147.5° C. (Mettler), and the analysis (percent by weight) was C, 65.45%; H, 9.57%; and O, 24.90% and showed the molecule to comprise C$_{34}$H$_{60}$O$_{10}$ (lysocellin, free acid).

EXAMPLE III

The sodium lysocellin made according to the method of Example I was used to make the crystalline zinc salt of lysocellin by the following method:

1.3 g of sodium lysocellin and 0.5 g of zinc acetate hydrate [Zn(Ac)$_2$.2H$_2$O] were added to 15 ml of acetone. The reactants were stirred at room temperature until all solids were in solution. Stirring was continued, and 30 ml of water was added dropwise to cause precipitation of the zinc salt complex of lysocellin. The crystalline precipitate was isolated and dried, redissolved in acetone and then recrystallized using the above procedure to yield the crystalline zinc lysocellin salt complex. Th melting point of this material was 109.5° C. (Mettler). The analysis was: C, 59.77%; H, 8.94%; O, 23.65%; Zn, 4.37%; indicating that two molecules of lysocellin are tied up with one zinc cation in the zinc salt complex as follows: (C$_{34}$H$_{59}$O$_{10}$)$_2$Zn.

EXAMPLE IV

Example III was repeated, except that zinc acetate hydrate was replaced by manganese acetate hydrate. The resulting manganese salt complex of lysocellin was amorphous, and had an analysis of 3.73% Mn, indicating that two molecules of lysocellin are tied up by one bivalent manganese cation as follows: (C$_{34}$H$_{59}$O$_{10}$)$_2$Mn.

EXAMPLE V

The method of Example III was repeated, except that the zinc acetate hydrate was replaced by cupric acetate hydrate [Cu(Ac)$_2$.2H$_2$O]. A mixture of 2.6 g of sodium lysocellin, 1.0 g cupric acetate hydrate and 50 ml of acetone was stirred until solution was complete. Stirring was continued, and water (2 col) was added dropwise. The copper salt complex of lysocellin was precipitated, isolated and recrystallized from aqueous acetone. The crystalline copper salt complex of lysocellin had a melting point of 119°-122° C. and it had 3.68% Cu, indicating there are two molecules of lysocellin tied up by one bivalent copper cation as follows: (C$_{34}$H$_{59}$O$_{10}$)$_2$Cu.

EXAMPLE VI

The in vitro rumen fermentation test described below can be used to accurately predict the improved feed utilization effects of test compounds fed to ruminants.

Microorganisms in the rumen of the animal ferment carbohydrates to produce monosaccharides and then degrade the monosaccharides to pyruvate compounds. Pyruvate is then metabolized by microbiological processes to either acetate or proprionate compounds. These compounds may be either acids or other forms of the radicals. Two acetate compounds may be combined still in the rumen to form butyrates.

The animal can utilize butyrate, propionate and acetate with differing degrees of efficiency. Butyrate is utilized most efficiently and acetate the least efficiently. The relative efficiency of butyrate is negated because it is made from acetate in the rumen.

One of the major inefficiencies in the rumen is in the manufacture of acetate. Since it is made by the degradation of a pyruvate molecule, each molecule of acetate produced is accompanied by a molecule of methane. Most of the methane produced is lost through eructation. Each molecule of butyrate used involves the loss of two molecules of methane with all its associated energy.

Thus the efficiency of carbohydrate utilization (carbohydrates being the major nutritive portion of animals' feed) can be increased by treatments which encourage the animal to produce propionate rather than acetate from the carbohydrates.

The efficiency of feed use can be effectively monitored by observing the production and concentration of propionate compounds in the rumen. If the animal is making more propionate, it will be found to be using its feed more efficiently. This efficiency is manifested by greater weight gains per feed intake, a reduction in energy losses by methane release, and economic advantages to the animal grower when the animal is sold for consumption.

Procedure

Rumen fluid was removed from a fistulated steer and strained through cheesecloth. An equal amount of pH 7 buffer was added to the strained rumen fluid. After layering occurred, the lower layer was saved and again diluted with an equal amount of butter.

Ten ml portions of the buffered rumen fluid were added to fermentation vessels containing 500 mg of fresh finely ground cattle ration, 1 mg of cellubiose, and amounts of the test compounds that resulted in a 5 ppm concentration.

The vessels were outfitted with one way gas valves and placed in an incubator shaker for 24 hours at 38° C. Fermentation was stopped by the addition of one ml of mercuric chloride.

The liquid was decanted and analyzed for volatile fatty acid by gas chromatography.

Conclusions

Changes in the acetate/propionate ratio caused by six forms of the polyether antibiotic lysocellin were determined by the above in vitro methods. The acetate/ propionate weight ratios given are from means of 10 tests for each compound.

| Negative Control | Positive Control Monensin | Example I Lysocellin Na | Example II Lysocellin Free Acid | Ex. III Lysocellin Zn | Example IV Lysocellin Mn | Example V Lysocellin Cu |
|---|---|---|---|---|---|---|
| 2.04 | 1.38 | 1.24 | 1.26 | 1.24 | 1.26 | 1.22 |

All forms of lysocellin tested were more effective than the positive control, monensin, in increasing the relative amount of propionate. From these results it can be concluded that all forms of lysocellin can be expected to improve feed efficiency when fed to ruminants. The fact that all forms of lysocellin performed substantially better than monensin would also indicate a possible effect as a growth promoter.

EXAMPLE VII

Twenty-five Columbia wether lambs were received and adapted to the basal ration set forth below in Table 1.

TABLE 1

Composition of the Basal Ration Wether Lamb Test

| | International Reference No. | Percent |
|---|---|---|
| Corn, cracked shelled | 4-20-931 | 68.7 |
| Alfalfa-whole corn plant, dehydrated[a] | | 20.0 |
| Soybean meal (44%) | 5-20-637 | 7.5 |
| Cane molasses | 4-04-696 | 2.0 |
| Limestone | 6-02-632 | 0.8 |
| Trace mineral salt[b] | | 0.6 |
| Vitamin premix[c] | | 0.4 |
| Calculated composition (as fed basis) | | |
| Crude protein | | 11.9 |
| Crude fiber | | 6.8 |
| Calcium | | 0.48 |
| Phosphorus | | 0.28 |
| Potassium | | 0.73 |
| Sulfur | | 0.27 |
| Digestible energy | | 3.08 Mcal/kg |

[a]Charles H. Schenk and Sons, Inc., Vincennes, Indiana. Guaranteed analysis: crude protein, min. 12.00%; crude fiber, max. 25.00%; fat, min. 1.50%; calcium, min. 0.75%, max. 0.87%; and phosphorus, min. 0.20%.
[b]Composition: NaCl, not >99.0%; not <0.35% Zn, 0.34% Fe, 0.200% Mn, 0.033% Cu, 0.077% I, and 0.005% Co.
[c]Provides per kg of diet: 2750 IU vitamin A; 700 IU vitamin D, and 10 IU vitamin E.

Animals

Six days after arrival, the lambs were weighed, tagged, treated with Tramisol wormer and vaccinated for both contagious ecthyma (soremouth) and *Clostridium perfringes* type D (overeating disease). Following adaptation, the lambs were reweighed. The lambs were then randomly assigned to five pens (five lambs per pen), providing approximately 1.42 sq. m. per animal. During the following eight-week experimental period, water and feed were available ad libitum.

Compounds Tested

There were four lysocellin materials tested, and a negative control. The test diets and control were each administered to five animals over the eight week test period. Each test ration contained the designated lysocellin compound at a level of 30g/ton.

Procedures

The lambs were weighed initially, and biweekly thereafter for the duration of the eight week experiment. The lambs were fasted for eighteen hours prior to weighing. Orts were weighed back at 3:00 P.M. the day prior to weighing the animals.

The effect of the dietary treatments is shown in Table 2 below:

TABLE 2

Effects of Addition to Ration of Various Lysocellin Materials in Wether Lambs

| Effect Observed | Control | Sodium Lysocellin | Zinc Lysocellin | Lysocellin (Free Acid) | Manganese Lysocellin |
|---|---|---|---|---|---|
| Avg. Daily Gain (kg/day/head) | 0.206 | 0.198 | 0.204 | 0.198 | 0.235 |
| Gain/Feed | 0.148 | 0.157 | 0.155 | 0.153 | 0.171 |

Of the above treatments, manganese lysocellin was most effective in increasing gain (growth promotion) and feed efficiency. Each of the test compositions showed some improvement in feed efficiency (gain/feed), and it is expected that when the dosage for each lysocellin material is optimized, all lysocellin materials will show an increase in gain (growth promotion) comparable, or better than, that observed for the manganese lysocellin material.

The zinc, manganese or copper lysocellin-containing feed composition is fed to cattle in amounts sufficient to provide from about 5 to 100 ppm of zinc, manganese or copper lysocellin in the rumen fluid. Administration of the zinc, manganese or copper lysocellin material in this manner serves to promote cattle growth by enhancing the efficiency with which the cattle so treated utilize their feed without suppressing appetite.

What is claimed is:

1. A process for promoting growth and enhancing feed efficiency of a food-producing mammal, which process comprises administering to a food-producing mammal in need of growth promotion and feed efficiency enhancement a growth-promoting and feed efficiency-enhancing amount of a lysocellin material selected from the group consisting of lysocellin, lysocellin free acid, and the physiologically acceptable salts thereof.

2. A process in accordance with claim 1 wherein the lysocellin material is selected from the soduim, zinc, manganese and copper lysocellin salts.

3. A process in accordance with claim 2 wherein the lysocellin material is administered parenterally.

4. A process in accordance with claim 1 wherein the food-producing mammal is a ruminant, and the lysocellin material comprises a metal salt complex which is administered as part of an animal feed composition containing from about 1 to 200 grams of the lysocellin material per ton of feed.

5. A process in accordance with claim 4, wherein the animal feed composition is fed to said ruminant at a rate sufficient to provide about 15 to 200 milligrams of the lysocellin material to said ruminant per day.

6. A process in accordance with claim 4 wherein the lysocellin material is a metal lysocellin material, and is administered in amounts sufficient to provide from about 5 to 100 ppm of metal lysocellin material in the rumen fluid contents.

7. A process in accodance with claim 6 wherein the lysocellin material is zinc lysocellin and is administered in amounts sufficient to provide from about 5 to 100 ppm of zinc lysocellin in the rumen fluid contents.

8. The process of claim 1 wherein the lysocellin material is zinc lysocellin.

9. The process of claim 1 wherein said mammal is a swine.

10. A process for promoting growth and enhancing feed efficiency of poultry which process comprises administering to poultry in need of growth promotion and feed efficiency enhancement, a growth-promoting and feed efficiency-enhancing amount of a lysocellin material selected from the group consisting of lysocellin, lysocellin free acid, and the physiologically acceptable salts thereof.

11. The process of claim 10 wherein the lysocellin material is selected from the soduim, zinc, manganese and copper salts.

12. The process of claim 10 wherein the lysocellin material comprises a metal salt complex which is administered as part of a feed composition containing from about 1 to 200 grams of the lysocellin material per ton of feed.

13. The process of claim 10 wherein lysocellin material is zinc lysocellin.

14. A process for promoting growth and enhancing feed efficiency of swine, which process comprises administering to swine a growth-promoting and feed efficiency-enhancing amount of a lysocellin material selected from the group consisting of lysocellin, lysocellin free acid, and the physiologically acceptable salts thereof.

15. A process for promoting growth and enhancing feed efficiency of a ruminant, which process comprises administering to a ruminant a growth-promoting and feed efficiency-enhancing amount of a lysocellin material selected from the group consisting of lysocellin, lysocellin free acid, and the physiologically acceptable salts thereof.

* * * * *

UNITED STATES PATENT AND TRADEMARK OFFICE
CERTIFICATE OF CORRECTION

PATENT NO. : 4,761,426

DATED : August 2, 1988

INVENTOR(S) : Jerome L. Martin

It is certified that error appears in the above-identified patent and that said Letters Patent is hereby corrected as shown below:

Column 3, line 56, delete growthpromoting" and substitute therefor -- growth-promoting --;

Column 4, line 31, delete "growthpromoting" and substitute therefor -- growth-promoting --;

Column 5, line 45, delete "Th" and substitute therefor -- The --;

Column 8, line 57, delete "soduim" and substitute therefor -- sodium --;

Column 9, line 8, delete "accodance" and substitute therefor -- accordance --;

Column 10, line 2, delete "soduim" and substitute therefor -- sodium --.

Signed and Sealed this

Eleventh Day of September, 1990

Attest:

HARRY F. MANBECK, JR.

*Attesting Officer*　　　　　　　*Commissioner of Patents and Trademarks*